United States Patent [19]
Durant

[11] 3,970,753
[45] July 20, 1976

[54] IMIDAZO[1,2-a]PYRIDINES
[75] Inventor: Graham John Durant, Welwyn Garden City, England
[73] Assignee: Smith Kline & French Laboratories Limited, Welwyn Garden City, England
[22] Filed: July 31, 1975
[21] Appl. No.: 600,664

Related U.S. Application Data
[62] Division of Ser. No. 476,345, June 5, 1974, abandoned.

[30] Foreign Application Priority Data
June 12, 1973 United Kingdom............... 27796/73

[52] U.S. Cl. .................................................. 424/263
[51] Int. Cl.² ......................................... A61K 31/44
[58] Field of Search .................................... 424/263

[56] References Cited
OTHER PUBLICATIONS
Almirante et al., Ball. Chim. Farm, vol. 105, pp. 32–44 (1966).
Almirante et al., Ball. Chim. Farm vol. 110, pp. 322–329 (1971).

Primary Examiner—Norman A. Drezin
Attorney, Agent, or Firm—Joan S. Keps; Richard D. Foggio; William H. Edgerton

[57] ABSTRACT
The compounds are imidazo [1,2-a]pyridines which possess activity similar to histamine, in particular, they are agonists of H-1 histamine receptors. A compound of this invention is 2-(2-aminoethyl)imidazo [1,2-a]pyridine.

5 Claims, No Drawings

IMIDAZO[1,2-A]PYRIDINES

This is a division of application Ser. No. 476,345, filed June 5, 1974, now abandoned.

This invention relates to imidazo [1,2,–a]pyridines and, in particular to 2-(2-aminoethyl)imidazo[1,2,–a]-pyridines and 2-(2-aminoethyl)-5,6,7,8-tetrahydroimidazo[1,2,–a]-pyridines. The invention also relates to pharmaceutical compositions and to methods of stimulating H-1 bistamine receptors with these compounds. The compounds of the invention can exist as addition salts but, for convenience, reference will be made throughout this specification to the parent compounds.

It has for long been postulated that many of the physiologically active substances within the animal body, in the course of their activity, combine with certain sites known as receptors. Such a substance is histamine and, since the actions of histamine are of more than one type, more than one type of receptor known as H-1 receptors and H-2 receptors have been identified (see Black et al Nature 1972, 236, 385). A number of compounds have been found which have similar activity to histamine and such compounds are known as histamine agonists. Many such compounds, like histamine, act at both H-1 and H-2 receptors but it is a feature of the present invention that their action is substantially specific to the H-1 receptors. This imparts to the compounds of the invention a peculiar pharmacological utility. For example they are of particular use in the diagnosis and/or treatment of certain vascular and vasomotor disorders.

Histamine itself may exist as one of the two possible tautomers shown in the following Formulae A and B:

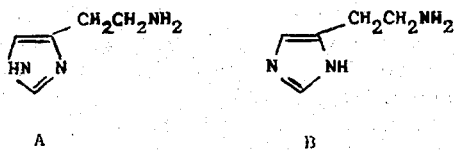

A      B and it has long been suggested that the characteristic pharmacological properties of histamine are associated with structures that have their origin in the tautomer of formula A and this tautomer may be looked upon as containing the obligatory structural requirements requisite for histamine-like biological activity (Niemann and Hays JACS 1942, 64, 2288).

The compounds of the present invention were therefore devised with the object of providing compounds which, although possessing a structural similarity to histamine, were capable of existing only in a form corresponding to that of the histamine tautomer of formula A.

According to the present invention, we provide compounds of the following formulae I (a) and I (b)

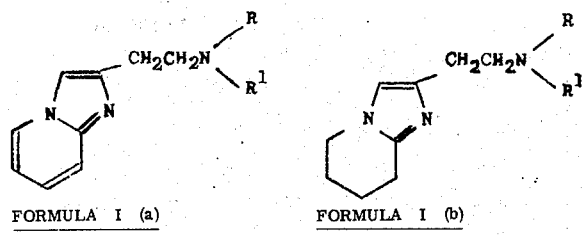

FORMULA I (a)      FORMULA I (b)

wherein R and R¹ may each be hydrogen, methyl or ethyl. Particularly useful compounds are those wherein R and R¹ are hydrogen or methyl.

The compounds of Formula I (a) wherein R and R¹ are both methyl or ethyl may be produced by the reaction of 2-amino-pyridine with a 1-halo-4-aminobutan-2-one of the following Formula II (a):

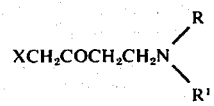

FORMULA II (a)

wherein X is halogen and R and R¹ are both methyl or ethyl whereas the compound of Formula I (a) wherein R and R¹ are both hydrogen is formed by first reacting 2-aminopyridine and a 1-halo-4-phthalimidobutan-2-one of Formula II (b).

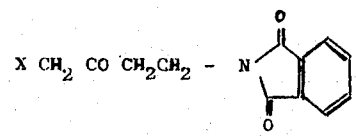

FORMULA II (b)

wherein X is halogen and then hydrolysing the resulting product.

Compounds wherein R is hydrogen and R¹ is methyl or ethyl may be formed by treatment of the compound wherein R and R¹ are both hydrogen with an acyl compound such as chloral, acetic anhydride or acetyl chloride and reduction of the product e.g., with lithium aluminium hydride.

The compounds of Formula I (b) are formed by the hydrogenation e.g., over a platinum catalyst, of the corresponding compound of Formula I (a).

As stated above the compounds of Formula I (a) and I (b) are specific histamine H-1 agonists, and thus have therapeutic value as alternatives to histamine, the clinical utility of which lies particularly in the diagnostic investigation of the vascular and vasomotor systems. They may also be of value in the treatment of disorders of these systems. The selective utility of our compounds as specific histamine H-1 agonists may be demonstrated by their ability, at concentrations of from 1 to $50.10^{-9}$ moles/ml., to stimulate contraction of an isolated piece of guineapig terminal ileum suspended in oxygenated Tyrode solution at 37°C in the presence of atropine (an H-1 receptor test system) whereas at doses of from 2 to 256 micromoles per kilogram intravenously, they do not stimulate the secretion of acid from the stomach of anaesthetised rats (an H-2 receptor test system). Since the above mentioned clinical utilities of histamine primarily make use of its activities at H-1 receptors the compounds of the present invention provide an alternative which is unencumbered by any, possibly undesirable, concomitant activity at the H-2 receptors.

Our invention also relates to pharmaceutical compositions comprising as the or an essential active ingredient at least one compound of Formula I (a) or I (b) in the basic form or in the form of an addition salt with a pharmaceutically acceptable acid and in association with a non-toxic diluent or carrier.

Advantageously the compositions will be made up in a dosage form appropriate to the desired mode of administration. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Other pharmacologically active compounds may in certain cases be included in the pharmaceutical compositions.

A wide variety of pharmaceutical forms can be employed: thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation will be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount. The route of administering may be internally e.g., orally or parenterally.

Preferably, each dosage unit will contain the active ingredient in an amount of from about 5 mg. to 100 mg. For diagnostic use, a single administration is usually sufficient but when used for treatment of vascular and vasomotor disorders the active ingredient will preferably be administered in equal doses from 1 to 3 times per day. The daily regimen in this latter case will preferably be from about 10 mg. to 300 mg.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefore. Such addition salts include those with hydrochloric, hydrobromic, hydriodic, sulphuric, picric and maleic acids and the addition salts with one of these acids may readily be converted to that with another. Such conversion may be effected by means of ion-exchange techniques.

A particularly useful method which also in many cases affects purification to a sufficient degree to allow the resultant solution of the addition salt to be used for pharmacological estimations involves the formation of the picrate salt and conversion therefrom to the chloride salt.

Advantageously the composition will be made up in a dosage form appropriate to the desired mode of administration for example, as a tablet, capsule or injectable solution.

EXAMPLE 1

2-(2-Aminoethyl)imidazo[1,2—a]pyridine dihydrochloride i. 1-Bromo-4-phthalimidobutan-2-one (23.6 g.) was added to a solution of 2-aminopyridine (7.6 g.) and sodium bicarbonate (6.8 g.) in dimethylformamide (100 ml.) and the mixture was heated at 100° for 1 hour. Cooling followed by addition to water and recrystallisation from ethanol afforded 2-(2-phthalimidoethyl)imidazo [1,2—a]-pyridine (13.4 g.) m.p. 181° – 181.5°.

(Found: C, 69.9; H, 4.5; N, 14.2%. $C_{17}H_{13}N_3O_2$ requires: C, 70.1; H, 4.5; N, 14.4%)

ii. A solution of the phthalimido derivative (15 g.) in 6N hydrochloric acid (400 ml.) was heated under reflux for 3 hours. Cooling, filtration from phthalic acid, followed by concentration and recrystallisation from ethanol afforded 2-(2-aminoethyl)imidazo [1,2—a]-pyridine dihydrochloride (11.6 g.) m.p. 285° – 290°.

(Found: C, 46.2; H, 5.4; N, 18.1; Cl, 30.2 $C_9H_{11}N_3.2$ HCl requires: C, 46.2; H, 4.5; N, 18.0; Cl, 30.3.)

EXAMPLE 2.

2-(2-Dimethylaminoethyl)imidazo [1,2—a]-pyridine dihydrobromide

A solution of 1-bromo-4-dimethylaminobutan-2-one (13.8 g.) and 2-aminopyridine (4.7 g.) in ethanol (50 ml.) was heated under reflux for 2 hours. Cooling filtration from 1-methylpyrrolidin-3-one methobromide (5.6 g.) followed by concentration and recrystallisation of the residue from methanol gave 2-(2-dimethylaminoethyl)-imidazo [1,2—a] pyridine dihydrobromide, m.p. 262° –264°.

(Found: C, 37.6; H, 4.9; N, 11.8. $C_{11}H_{15}N_3$. 2 HBr requires: C, 37.6; H, 4.9; N, 12.0)

EXAMPLE 3.

2-(2-Aminoethyl)-5,6,7,8-tetrahydromidazo [1,2—a]pyridine dinitrate

A solution of 2-(2-aminoethyl)imidazo [1,2—a]pyridine dihydrochloride (2.2 g.) in ethanol (150 ml.) containing hydrochloric acid (5 ml.) was hydrogenated at room temperature over a platinum catalyst until the uptake of hydrogen was complete. Filtration and concentration afforded a hygroscopic hydrochloride, which was treated with silver nitrate to furnish 2-(2-aminoethyl)-5,6,7,8-tetrahydroimidazo [1,2—a]pyridine dinitrate (1.1 g.), m.p. 180° – 182.5° (from ethanol).

EXAMPLE 4

2-(2-Dimethylaminoethyl)-5,6,7,8-tetrahydroimidazo [1,2—a] pyridine dinitrate

When 2-(2-dimethylaminoethyl)imidazo [1,2—a]-pyridine dihydrobromide is used as the starting material in the process of Example 3, the title compound is produced.

EXAMPLE 5

2-(2-Methylaminoethyl)imidazo [1,2—a]pyridine dihydrochloride

To a stirred solution of 2-(2-aminoethyl)imidazo [1,2—a] pyridine in chloroform chloral was added dropwise and stirring continued at room temperature for an hour. A solid precipitate was filtered off and recrystallised to give 2-(2-formamidoethyl)imidazo [1,2—a]pyridine. The 2-(2-formamidoethyl)imidazo [1,2—a]pyridine was gradually added to a slurry of lithium aluminium hydride in anhydrous tetrahydrofuran and the resultant suspension heated under reflux for 3 hours. By extracting the reaction mixture with dilute hydrochloric acid there was isolated 2-(2-methylaminoethyl)imidazo [1,2—a]pyridine dihydrochloride.

EXAMPLE 6

2-(2-Diethylaminoethyl)imidazo [1,2—a]pyridine dihydrobromide

Reaction of 1-bromo-4-diethylaminobutan-2-one and 2-aminopyridine by the procedure of Example 2 yields the title product.

EXAMPLE 7

A solution of 2-(2-aminoethyl)imidazo [1,2—a]pyridine dihydrochloride in ethanol is absorbed onto an ion-exchange column in OH-form. Elution with ethanol/ether and evaporation of the solvent afforded the free base. Similarly the free base may be obtained from the salts produced in any one of Examples 2 to 6.

EXAMPLE 8

| Ingredients | Amounts |
|---|---|
| 2-(2-Aminoethyl)imidazo [1,2-a]pyridine dihydrochloride | 50 mg. |
| Sucrose | 75 mg. |
| Starch | 25 mg. |
| Talc | 5 mg. |
| Stearic Acid | 2 mg. |

The ingredients are screened, mixed and filled into a hard gelatin capsule.

I claim:
1. A method of stimulting H-1 histamine receptors which comprises administering to an animal in need thereof, in an effective amount to stimulate said receptors, an imidazo-pyridine compound of the formula:

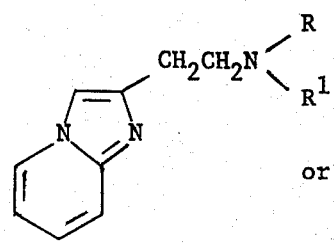

or

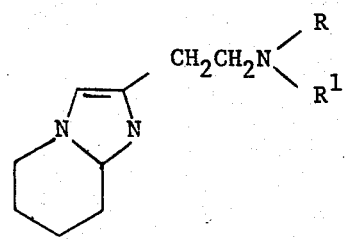

wherein R and $R^1$ may each be hydrogen, methyl or ethyl or a pharmaceutically acceptable acid addition salt thereof.

2. A method of claim 1 in which the imidazo-pyridine compound is 2-(2-aminoethyl)imidazo[1,2—a]pyridine.

3. A method of claim 1 in which the imidazo-pyridine compound is 2-(2-dimethylaminoethyl)imidazo[1,2—a]pyridine.

4. A method of claim 1 in which the imidazo-pyridine compound is 2-(2-aminoethyl)-5,6,7,8-tetrahydroimidazo[1,2—a]-pyridine.

5. A method of claim 1 in which the imidazo-pyridine compound is administered in a daily dosage regimen of from about 10 mg. to 300 mg.

* * * * *

UNITED STATES PATENT AND TRADEMARK OFFICE
CERTIFICATE OF CORRECTION

PATENT NO. : 3,970,753
DATED : July 20, 1976
INVENTOR(S) : Graham John Durant

It is certified that error appears in the above-identified patent and that said Letters Patent are hereby corrected as shown below:

Column 1, line 10, "bistamine" should read -- histamine --.

Column 5, line 37, "stimulting" should read -- stimulating --.

Column 6, lines 12-20, the formula should appear as follows:

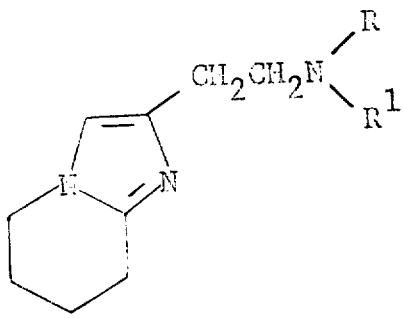

Signed and Sealed this

Twenty-sixth Day of October 1976

[SEAL]

Attest:

RUTH C. MASON
Attesting Officer

C. MARSHALL DANN
Commissioner of Patents and Trademarks